(12) United States Patent
Komann et al.

(10) Patent No.: US 12,286,265 B2
(45) Date of Patent: Apr. 29, 2025

(54) HOLDING STRUCTURE FOR READY-TO-USE CONTAINERS

(71) Applicant: SCHOTT Pharma Schweiz AG, St. Gallen (CH)

(72) Inventors: Christian Komann, Speicher (CH); Petra Vilt, Herisau (CH); Ugljesa Babic, Winterthur (CH); Yannick Dähler, Wil SG (CH)

(73) Assignee: SCHOTT Pharma Schweiz AG, St. Gallen (CH)

( * ) Notice: Subject to any disclaimer, the term of this patent is extended or adjusted under 35 U.S.C. 154(b) by 0 days.

(21) Appl. No.: 18/738,391

(22) Filed: Jun. 10, 2024

(65) Prior Publication Data

US 2024/0327055 A1    Oct. 3, 2024

Related U.S. Application Data

(63) Continuation of application No. 17/972,090, filed on Oct. 24, 2022, now Pat. No. 12,071,271.

(30) Foreign Application Priority Data

Oct. 25, 2021    (EP) .................................... 21204557

(51) Int. Cl.
  *B65D 1/36*    (2006.01)
  *A61J 1/16*    (2023.01)
  *A61M 5/00*    (2006.01)

(52) U.S. Cl.
  CPC ...... *B65D 1/36* (2013.01); *A61J 1/16* (2013.01); *A61M 5/008* (2013.01)

(58) Field of Classification Search
  CPC .............. B65D 1/36; A61J 1/16; A61M 5/008
  See application file for complete search history.

(56) References Cited

U.S. PATENT DOCUMENTS 3,056,523 A    10/1962  Reifers
8,505,723 B2 *  8/2013  Clark ................... B65D 5/503
                                         206/443

(Continued)

FOREIGN PATENT DOCUMENTS

WO    2012/126582 A1    9/2012
WO    2016166769 A1    10/2016

OTHER PUBLICATIONS

European Communication Pursuant to Article 94(3) EPC dated May 13, 2022 for European Patent Application No. 21 204 557.9 (6 pages).

*Primary Examiner* — Anita M King
(74) *Attorney, Agent, or Firm* — TAYLOR & EDELSTEIN

(57) ABSTRACT

A holding structure for simultaneously holding containers for pharmaceutical, medical, or cosmetic compositions includes: at least ten receptacles for receiving the containers and being formed by side walls; a flat base frame including a central recess; first webs running parallel to each other in a first direction across the central recess; second webs running parallel to each other in a second direction across the central recess, the first webs and the second webs being arranged such that the first webs and the second webs form the side walls, each of the first webs and the second webs being formed as a continuous beam having a maximum waviness $w_{max}$ of 4.0 mm, the holding structure including a warpage of less than 2.0 mm as determined by a test method before steam sterilization, the warpage corresponding to a bending after the holding structure has been prepared and is empty.

9 Claims, 13 Drawing Sheets

(56) References Cited

U.S. PATENT DOCUMENTS

| | | |
|---|---|---|
| 8,800,800 B2 | 8/2014 | Gerner |
| 9,963,259 B2 | 5/2018 | Deutschle |
| 11,472,602 B2 | 10/2022 | Komann |
| 11,794,974 B2 | 10/2023 | Komann |
| 2014/0027333 A1 | 1/2014 | Pawlowski |
| 2017/0183113 A1 | 6/2017 | Deutschle et al. |
| 2019/0256266 A1* | 8/2019 | Komann ............... B65D 25/108 |
| 2020/0156840 A1 | 5/2020 | Komann et al. |
| 2021/0220547 A1 | 7/2021 | Sonoyama et al. |
| 2022/0097914 A1* | 3/2022 | Kücük ............... B65D 77/2024 |

* cited by examiner

HOLDING STRUCTURE FOR READY-TO-USE CONTAINERS

CROSS REFERENCE TO RELATED APPLICATIONS

This is a continuation application of U.S. patent application Ser. No. 17/972,090, entitled "HOLDING STRUCTURE FOR READY-TO-USE CONTAINERS", filed Oct. 24, 2022, which is incorporated herein by reference. U.S. patent application Ser. No. 17/972,090 claims priority to European patent application no. 21 204 557.9, entitled "HOLDING STRUCTURE FOR READY-TO-USE CONTAINERS", filed Oct. 25, 2021, which is incorporated herein by reference.

BACKGROUND OF THE INVENTION

1. Field of the Invention

The present invention relates to a holding structure for simultaneously holding a plurality of primary packaging containers for pharmaceutical, medical or cosmetic compositions, wherein the holding structure includes a plurality of receptacles for receiving the primary packaging containers and wherein the receptacles are formed by peripherally formed side walls. The present invention also relates to a transport or packaging container, to the use of a holding structure and to a plurality of holding structures.

2. Description of the Related Art

Medicament containers, such as, for example, syringes, vials, ampoules or cartridges, are widely used as containers for storing medical, pharmaceutical or cosmetic preparations for administration in liquid form, in particular in pre-dosed quantities. These medicament containers generally have a cylindrical shape, can be produced from plastics or from glass and can be obtained in a cost-effective manner in large numbers. In this respect, the containers are increasingly being delivered in holding structures in a predetermined geometric arrangement to a pharmaceuticals manufacturer or to a subsequent processing operation and are further processed while the containers are held or received in the holding structure. For this purpose, cost-effective and durable holding structures are required in which the containers are held or received in an arrangement which takes up the least possible space.

An example of a holding structure suitable to hold pre-filled cartridges is disclosed in WO 2016/166769 A1. The holding structures includes a plurality of tubular receptacles disposed in the same regular arrangement, which accommodate a plurality of cartridges, wherein retaining protrusions are formed at the bottom ends of the receptacles protruding inward and the sealed cartridges are accommodated upside-down in the receptacles so that the shoulder portions of the sealed cartridges are supported on the retaining protrusions of the receptacle.

WO 2012/126582 A1 discloses a further holding structure for syringe bodies, having a plate-shaped carrier on which there are formed a plurality of cylindrical receptacles having peripherally formed side walls. The syringe bodies rest by way of their holding flanges on the upper ends of the cylindrical receptacles. In order to stiffen the carrier, the cylindrical receptacles are connected to one another via connecting webs on the lower side of the carrier.

In order to make filling of the containers under sterile conditions as economical as possible, these containers are increasingly delivered by the manufacturer of the containers to the pharmaceutical filling company in a sterile packaging, so that the pharmaceutical filling company does not need to clean and sterilize the containers. For this purpose, the containers need to be unpacked under sterile conditions at the pharmaceutical filling company, for example a pharmaceutical company, and are then processed further. Increasingly, production concepts are also used wherein the containers remain in the above described holding structures of the sterile packaging during the filling process and wherein the containers are filled while they are arranged in the holding structure, which is part of the sterile packaging. In addition to the actual filling process, other sub-processes such as weighing, placing of stoppers, lyophilization and final sealing of the containers with the stoppers may also be carried out, while the containers are supported in the holding structure. This results in numerous additional requirements on the holding structure, especially with regard to the accuracy of the positions of the containers in the holding structure.

When using the above described holding structures known from the prior art to accommodate long and slim containers (such as syringes or cartridges) in a high packaging density, it has been observed that certain process steps, such as filling with a pharmaceutical composition or closing with a stopper, can often not be carried out in automatic systems with the desired precision at a simultaneously high cycle frequency. Particularly in the case of containers with a comparatively high dead weight, such as filled glass syringes or filled glass cartridges, it has been observed that the precise setting of stoppers after the filling process to close the containers at a high cycle frequency (i.e., at a high number of holding structures loaded with the containers that are to be filled and closed per unit of time in an automatic filling device) is in particular in need of improvement. This applies in particular to holding structures made of thermoplastic polymers that have previously been sterilized by way of steam and thus under thermal stress.

There is thus further need for improvement in the production of holding structures of the aforementioned type.

What is needed in the art is an improved holding structure for simultaneously holding a plurality of containers for substances for pharmaceutical, medical or cosmetic applications that can be produced in a simple and cost-effective manner and that allow an advantageously high packing density of the containers, particularly of containers having a high dead weight such as glass syringes or glass cartridges. In addition, the holding structure should enable such containers to be accommodated in a density as high as possible and—while they are accommodated in the holding structure—to be filled and subsequently to be closed by inserting a stopper into the open end of the containers as uniformly as possible in as high a cycle frequency as possible. This should particularly hold true for holding structures which are based on thermoplastic polymers and which have previously been sterilized at elevated temperatures, particularly at temperatures of around 121° C. for at least using steam. Moreover, the holding structures—while being characterized by the aforementioned advantageous properties—should at the same time optionally also be characterized by a dead weight as low as possible.

SUMMARY OF THE INVENTION

The present invention provides a 1st embodiment of a holding structure 1 for simultaneously holding a plurality of primary packaging containers for pharmaceutical, medical or cosmetic compositions;

wherein the holding structure includes n receptacles for receiving the primary packaging containers, wherein n is an integer having a value of at least 10 and wherein the receptacles are formed by peripherally formed side walls;

wherein the holding structure includes:
- a flat base frame with a maximum length $L_x$ and a maximum width $L_y$, the flat base frame having a first side and a second side and including a central recess with a length $L'_x$ and a width $L'_y$;
- a plurality of first webs running parallel to each other in a first direction across the central recess;
- a plurality of second webs running parallel to each other in a second direction across the central recess;
- wherein the first and seconds webs are arranged in such a manner that they form the side walls of the receptacles;

wherein each of the first and the second webs is in the form of a continuous beam having a maximum waviness of $w_{max}$ of less than 4.0 mm, optionally of less than 3.8 mm, optionally of less than 3.6 mm, optionally of less than 3.4 mm, optionally of less than 3.2 mm, optionally of less than 3.0 mm, optionally of less than 2.8 mm, optionally of less than 2.6 mm, optionally of less than 2.4 mm, optionally of less than 2.2 mm, optionally of less than 2.0 mm, optionally of less than 1.8 mm, optionally of less than 1.6 mm, optionally of less than 1.4 mm, optionally of less than 1.2 mm, optionally of less than 1.0 mm, optionally of less than 0.8 mm, optionally of less than 0.6 mm, optionally of less than 0.4 mm and optionally of less than 0.2 mm, wherein a maximum waviness $w_{max}$ of 0 mm is optional (i.e., it is optional that the first and second webs are in the form of substantially straight beams).

A "primary packaging container" in the sense of the present invention is a container that can be filled with pharmaceutical, medical or cosmetic compositions, such as a syringe body, a vial, an ampoule or a cartridge, optionally a syringe body or a cartridge and optionally a syringe body, particularly a glass syringe body or a polymer syringe body. These containers optionally include a rotationally symmetrical body having a first end and a second end, one of these ends, optionally the lower end, being closed when the containers are inserted into the holding structure and the other end, optionally the upper end, being open so that the containers, while being held in the holding structure, can optionally be filled with a pharmaceutical, medical or cosmetic composition via the upper end.

In an optional embodiment of holding structure 1 according to the present invention the holding structure further includes:
- an outer frame that protrudes from the flat base frame on the first side, on the second side or on both sides and that is connected with the flat base frame in such a manner that the outer frame surrounds the central recess of the base frame;

wherein each of the first and the second webs is connected to the outer frame at the respective end of the web. This optional embodiment is a $2^{nd}$ embodiment of holding structure 1 according to the present invention, that optionally depends on the $1^{st}$ embodiment of the invention.

According to a particular embodiment of the above-described $2^{nd}$ embodiment of holding structure 1 according to the present invention the outer frame includes a top edge, a bottom edge, a first side edge and a second side edge, these edges being connected with each other in such a manner that they form a continuous outer frame, wherein each of the first and the second webs enclose an angle $\alpha$ with the edges of the outer frame and wherein $\alpha$ is in the range from 0 to 90°, optionally in the range from 20 to 80°, optionally in the range from 30 to 70°, optionally in the range from 40 to 60° and optionally in the range from 45 to 55°.

According to a further particular embodiment of the above-described $2^{nd}$ embodiment of holding structure 1 according to the present invention the bars of the outer frame have a wall thickness in the range from 0.5 to 4.0 mm, optionally in the range from 0.8 to 3.5 mm, optionally in the range from 1.2 to 3.0 mm, and optionally in the range from 1.5 to 2.5 mm. The height of the bars of the outer frame is optionally in the range from 5 to 35 mm, more optionally in the range from 10 to 30 mm, even more optionally in the range from 12 to 28 mm and most optionally in the range from 15 to 25 mm.

According to a further particular embodiment of the above-described $2^{nd}$ embodiment of holding structure 1 according to the present invention the maximum area that is spanned by the flat base frame is greater than the area that spanned by the outer frame. In this context it is particularly optional that the holding structure further includes:
- stabilizing elements by way of which the outer frame is connected to the flat base frame.

Optionally, these stabilizing elements are in the form of wings, which are connected to the edges of the outer frame on one side and to the flat base frame on an adjacent side of the stabilizing element. In this context, it is also optional that each edge of the outer frame is connected to the flat base frame via at least two such stabilizing elements. In this context it is also optional that the holding device further includes access openings that enable the holding structure to be gripped or guided. Optionally, the holding device includes two such access openings recessed into the flat base frame on opposite sides of the holding device.

In a further optional embodiment of holding structure 1 according to the present invention the first and the second webs have a wall thickness in the range from 0.1 to 4.0 mm, optionally in the range from 0.2 to 3.5 mm, optionally in the range from 0.3 to 2.0 mm, and optionally in the range from 0.5 to 1.0 mm. The height of the first and the second webs is optionally in the range from 5 to 35 mm, optionally in the range from 10 to 30 mm, optionally in the range from 12 to 28 mm, and optionally in the range from 15 to 25 mm. This optional embodiment is a $3^{rd}$ embodiment of holding structure 1 according to the present invention, that optionally depends on the $1^{st}$ or the $2^{nd}$ embodiment of the invention.

In a further optional embodiment of holding structure 1 according to the present invention the flat base frame has a thickness in the range from 0.5 to 3.0 mm, optionally in the range from 0.8 to 2.5 mm, optionally in the range from 1.0 to 2.0 mm, and optionally in the range from 1.2 to 1.6 mm. This optional embodiment is a $4^{th}$ embodiment of holding structure 1 according to the present invention, that optionally depends on any of the $1^{st}$ to the $3^{rd}$ embodiment of the invention.

In a further optional embodiment of holding structure 1 according to the present invention the holding structure has an area moment of inertia I of at least 100 mm$^4$, optionally at least 200 mm$^4$, optionally at least 300 mm$^4$, and optionally at least 400 mm$^4$. This optional embodiment is a $5^{th}$ embodiment of holding structure 1 according to the present invention that optionally depends on the any of the $1^{st}$ to the $4^{th}$ embodiment of the invention.

In a further optional embodiment of holding structure 1 according to the present invention the holding structure has received n primary packaging containers, optionally n primary packaging containers selected from the group consisting of syringe bodies, vials, ampoules or cartridges, optionally n syringe bodies or cartridges and optionally n syringe bodies, particularly n glass syringe bodies or n polymer syringe bodies. The n primary packaging containers can be empty (i. e. they do not include any pharmaceutical, medical or cosmetic compositions) or they can be at least partially filled with a pharmaceutical, medical or cosmetic composition. This optional embodiment is a $6^{th}$ embodiment of holding structure 1 according to the present invention that optionally depends on any of the $1^{st}$ to the $5^{th}$ embodiment of the invention.

In a further optional embodiment of holding structure 1 according to the present invention the holding structure has, when being loaded with n empty or at least partially filled receptacles having a total weight of up to 400 g, a deflection D as determined by the test method disclosed herein of less than 0.25 mm, optionally less than 0.22 mm and optionally less than 0.18 mm. This optional embodiment is a $7^h$ embodiment of the holding structure according to the present invention that optionally depends on anyone of the $1^{st}$ to the $6^{th}$ embodiment of the invention.

In a further optional embodiment of holding structure 1 according to the present invention the holding structure has, when being loaded with n empty or at least partially filled receptacles having a total weight of up to 800 g, a deflection D' as determined by the test method disclosed herein of less than 0.4 mm, optionally less than 0.37 mm and optionally less than 0.34 mm. This optional embodiment is an $8^{th}$ embodiment of the holding structure according to the present invention that optionally depends on anyone of the $1^{st}$ to the $7^{th}$ embodiment of the invention.

In a further optional embodiment of holding structure 1 according to the present invention the holding structure has, when being loaded with n empty or at least partially filled receptacles having a total weight of up to 1,100 g, a deflection D" as determined by the test method disclosed herein of less than 0.5 mm, optionally less than 0.47 mm, and optionally less than 0.44 mm. This optional embodiment is a $9^{th}$ embodiment of holding structure 1 according to the present invention that optionally depends on the anyone of the $1^{st}$ to the $8^{th}$ embodiment of the invention.

In a further optional embodiment of holding structure 1 according to the present invention the outer frame and the first and the second webs have a height in the range from 15 to 25 mm, optionally in the range from 16.5 to 22.5 mm and optionally in the range from 17 to 20 mm. This optional embodiment is a $10^{th}$ embodiment of holding structure 1 according to the present invention that optionally depends on any of the $2^{nd}$ to the $9^{th}$ embodiments of the invention.

In a further optional embodiment of holding structure 1 according to the present invention $L_x$ is in the range from 200 to 260 mm, optionally in the range from 220 to 240 mm, and wherein $L_y$ is in the range from 170 to 230 mm, optionally in the range from 190 to 210 mm. This optional embodiment is an $11^{th}$ embodiment of holding structure 1 according to the present invention that optionally depends on any of the $1^{st}$ to the $10^{th}$ embodiments of the invention.

In a further optional embodiment of holding structure 1 according to the present invention $L'_x$ is in the range from 170 to 230 mm, optionally in the range from 190 to 210 mm, and wherein $L'_y$ is in the range from 140 to 200 mm, optionally in the range from 160 to 180 mm. This optional embodiment is a $12^{th}$ embodiment of holding structure 1 according to the present invention that optionally depends on any of the $1^{st}$ to the $11^{th}$ embodiments of the invention.

In a further optional embodiment of holding structure 1 according to the present invention the holding structure in the empty state has a mass per unit area of less than 0.5 $g/cm^2$, optionally of less than 0.4 $g/cm^2$ and more optionally of less than 0.3 $g/cm^2$. This optional embodiment is a $13^{th}$ embodiment of holding structure 1 according to the present invention that optionally depends on any of the $1^{st}$ to the $12^{th}$ embodiments of the invention.

In a further optional embodiment of holding structure 1 according to the present invention the holding structure is based on, optionally is made of, a thermoplastic polymer, optionally a thermoplastic polymer having a melting point in the range from 100 to 300°. In this context it is particularly optional that the thermoplastic material is selected from the group consisting of polyether ether ketones (PEEK), polyphenylsulfones (PPSU), polyacetale homo- or copolymers (POM-H or POM-C), polypropylenes (PP), polycarbonates, polystyrenes, polyamides, polyethylene terephthalates, acrylonitrile/butadiene/styrene-copolymers or a mixture of at least two of these polymers, wherein these polymers can also be filled with fillers such as calcium carbonate, kaolin, carbon black, carbon fibers, aluminum hydroxide, aluminum trihydrate, talc, dolomite, barium ferrite, wollastonite, wood flour, glass fibers, nanoclay, starch (crystalline and amorphous), calcium sulfate, glass spheres, mica, silica, feldspar, nephelline, graphite, boron nitride, silicon carbide, silicon nitride, aluminum oxide, titanium dioxide, zinc oxide, iron oxide, magnesium oxide, zirconium oxide or a mixture of at least two of these fillers. Particularly optional is the use of polypropylene or of a polypropylene filled with one of the above-mentioned fillers. Also suitable is a polymer selected from the group consisting of olefin copolymers, cyclic olefin polymers or a mixture thereof. This optional embodiment is a $14^{th}$ embodiment of holding structure 1 according to the present invention, that optionally depends on any of the $1^{st}$ to the $13^{th}$ embodiments of the invention.

In a further optional embodiment of holding structure 1 according to the present invention the holding structure is formed in one piece by injection moulding, by way of 3D-printing or by way of a combination of these approaches. This optional embodiment is a $15^{th}$ embodiment of holding structure 1 according to the present invention, that optionally depends on any of the $1^{st}$ to the $14^{th}$ embodiments of the invention.

In a further optional embodiment of holding structure 1 according to the present invention:
  if the holding structure is loaded with n empty primary packaging container each having a weight $m_0$, if $m_1$ is the weight of the empty holding structure, $m_1/(n \times m_0)$ is less than 0.24, optionally less than 0.22, optionally less than 0.20, optionally less than 0.18, optionally less than 0.15, and optionally less than 0.12. This optional embodiment is a $16^{th}$ embodiment of holding structure 1 according to the present invention that optionally depends on any of the $1^{st}$ to the $15^{th}$ embodiments of the invention.

In a further optional embodiment of holding structure 1 according to the present invention the holding structure is characterized by a warpage as determined before steam sterilization by the test method disclosed herein of less than 2.0 mm, optionally less than 1.0 mm, and optionally less than 0.5 mm. This optional embodiment is a $17^{th}$ embodiment of holding structure 1 according to the present invention, that optionally depends on the any of the $1^{st}$ to the $16^{th}$ embodiments of the invention. The warpage corresponds to the bending of an (empty) holding structure after it has been prepared, for example by way of 3D-printing, injection molding or by way of a combination of these approaches.

In a further optional embodiment of holding structure 1 according to the present invention the holding structure is characterized by a warpage as determined after steam sterilization at 122° C. for 22 min by the test method disclosed herein of less than 4.0 mm, optionally less than 2.0 mm, and optionally less than 1.0 mm. This optional embodiment is an $18^{th}$ embodiment of holding structure 1 according to the present invention, that optionally depends on the any of the $1^{st}$ to the $17^{th}$ embodiments of the invention.

In a further optional embodiment of holding structure 1 according to the present invention the holding structure is characterized by a limit expansion as determined by the test method disclosed herein of less than 1%, optionally less than 0.5%, and optionally less than 0.1%. This optional embodiment is a $19^{th}$ embodiment of holding structure 1 according to the present invention, that optionally depends on any of the $1^{st}$ to the $18^{th}$ embodiments of the invention.

In a further optional embodiment of holding structure 1 according to the present invention the holding structure is a sterile holding structure that has been sterilized with steam at a temperature in the range from 120 to 130° C., optionally 121 to 128° C., and optionally 122 to 125° C. for 10 to 60 minutes, optionally for 15 to 40 minutes and optionally from 20 to 30 minutes. This optional embodiment is a $20^{th}$ embodiment of holding structure 1 according to the present invention, that optionally depends on any of the $1^{st}$ to the $19^{th}$ embodiments of the invention.

In a further optional embodiment of holding structure 1 according to the present invention the primary packaging container that can be held (or, in case of the $6^{th}$ optional embodiment, that is held by the holding structure) is a container selected from the group consisting of a syringe body, a vial, an ampoule and a cartridge, wherein a syringe body is particularly optional. In this context it is also optional that the primary packaging containers, optionally the syringe body, is based on, optionally is made of, glass or a polymer (and is thus a glass syringe body). More optionally, the primary packaging container is a glass syringe body on whose distal end there is formed an ejection opening and, on the opposite end, a filling opening for filling and subsequently receiving a plunger or stopper, wherein at this opposite end a widened flange is provided. In this context it is also optional that the syringe bodies, optionally the glass syringe bodies or a polymer syringe body, are received upside down in the receptacles of the holding structure according to the present invention, wherein the widened flange lies on the upper ends of the side walls. This optional embodiment is a $21^{st}$ embodiment of holding structure 1 according to the present invention, that optionally depends on any of the $1^{st}$ to the $20^{th}$ embodiments of the invention.

According to a first particular embodiment of the above-described $21^{st}$ embodiment of holding structure 1 according to the present invention, the primary packaging container is a glass syringe body and the following conditions are fulfilled:
  i) the syringe body has a nominal volume in the range from 0.3 to 0.7 ml, optionally in the range from 0.4 to 0.6 ml, and optionally in the range from 0.45 to 0.55 ml;
  ii) the syringe body has a barrel length GL in the range from 64 to 84 mm, optionally in the range from 68 to 80 mm, and more optionally in the range from 72 to 76 mm;
  iii) the syringe body has an outside diameter OD in the range from 5 to 9 mm, optionally in the range from 6 to 8 mm, and more optionally in the range from 6.5 to 7.5 mm.

According to a second particular embodiment of the above-described $21^{st}$ embodiment of holding structure 1 according to the present invention, the primary packaging container is a glass syringe body and the following conditions are fulfilled:
  i) the syringe body has a nominal volume in the range from 0.9 to 1.1 ml, optionally in the range from 0.95 to 1.05 ml, and optionally in the range from 0.99 to 1.01 ml;
  ii) the syringe body has a barrel length GL in the range from 70 to 90 mm, optionally in the range from 75 to 85 mm, and optionally in the range from 78 to 82 mm;
  iii) the syringe body has an outside diameter OD in the range from 7 to 9 mm, optionally in the range from 7.5 to 8.5 mm, and optionally in the range from 7.8 to 8.2 mm.

According to a third particular embodiment of the above-described $21^{st}$ embodiment of holding structure 1 according to the present invention, the primary packaging container is a glass syringe body or a polymer syringe body, particularly a syringe body made from a cyclic olefin copolymer (COC) such as TopPac® (Schott, Germany), and the following conditions are fulfilled:
  i) the syringe body has a nominal volume in the range from 0.3 to 1.5 ml, optionally in the range from 0.4 to 1.3 ml, and optionally in the range from 0.5 to 1.0 ml;
  ii) the syringe body has a barrel length GL in the range from 40 to 85 mm, optionally in the range from 50 to 80 mm, and optionally in the range from 54 to 73 mm;
  iii) the syringe body has an outside diameter OD in the range from 8 to 12 mm, optionally in the range from 9 to 11.5 mm, and optionally in the range from 9.4 to 11 mm.

According to a fourth particular embodiment of the above-described $21^{st}$ embodiment of holding structure 1 according to the present invention, the primary packaging container is a polymer syringe body, particularly a syringe body made from a cyclic olefin copolymer (COC) such as TopPac® (Schott, Germany), and the following conditions are fulfilled:
  i) the syringe body has a nominal volume in the range from 1.8 to 3.5 ml, optionally in the range from 2 to 3.3 ml, and optionally in the range from 2.2 to 3 ml;
  ii) the syringe body has a barrel length GL in the range from 63 to 83 mm, optionally in the range from 68 to 78 mm, and optionally in the range from 72 to 74 mm;
  iii) the syringe body has an outside diameter OD in the range from 10.5 to 12.5 mm, optionally in the range from 11 to 12 mm, and optionally in the range from 11.4 to 11.6 mm.

According to a fifth particular embodiment of the above-described $21^{st}$ embodiment of holding structure 1 according to the present invention, the primary packaging container is a glass syringe body and the following conditions are fulfilled:
  i) the syringe body has a nominal volume in the range from 2.5 to 3.5 ml, optionally in the range from 2.8 to 3.2 ml, and optionally in the range from 2.9 to 3.1 ml;
  ii) the syringe body has a barrel length GL in the range from 75 to 95 mm, optionally in the range from 80 to 90 mm, and optionally in the range from 83 to 87 mm;

iii) the syringe body has an outside diameter OD in the range from 13 to 16 mm, optionally in the range from 14 to 15 mm, and optionally in the range from 14.4 to 14.6 mm.

According to a sixth particular embodiment of the above-described 21$^{st}$ embodiment of holding structure 1 according to the present invention, the primary packaging container is a polymer syringe body, optionally a syringe body made from a cyclic olefin copolymer (COC) such as TopPac® (Schott, Germany), and the following conditions are fulfilled:
  i) the syringe body has a nominal volume in the range from 3 to 12 ml, optionally in the range from 4 to 11 ml, and optionally on the range from 5 to 10 ml;
  ii) the syringe body has a barrel length GL in the range from 95 to 115 mm, optionally in the range from 100 to 112 mm, and optionally in the range from 104 to 108 mm;
  iii) the syringe body has an outside diameter OD in the range from 13 to 17 mm, optionally in the range from 14 to 16 mm, and optionally in the range from 14.8 to 15.2 mm.

According to a seventh particular embodiment of the above-described 21$^{st}$ embodiment of holding structure 1 according to the present invention, the primary packaging container is a polymer syringe body, optionally a syringe body made from a cyclic olefin copolymer (COC) such as TopPac® (Schott, Germany), and the following conditions are fulfilled:
  i) the syringe body has a nominal volume in the range from 15 to 25 ml, optionally in the range from 15.5 to 22.5 ml, and more optionally on the range from 19 to 21 ml;
  ii) the syringe body has a barrel length GL in the range from 95 to 115 mm, optionally in the range from 100 to 112 mm, and more optionally in the range from 104 to 108 mm;
  iii) the syringe body has an outside diameter OD in the range from 16 to 20 mm, optionally in the range from 17 to 19 mm, and optionally in the range from 17.8 to 18.2 mm.

According to an eighth particular embodiment of the above-described 21$^{st}$ embodiment of holding structure 1 according to the present invention, the primary packaging container is a polymer syringe body, optionally a syringe body made from a cyclic olefin copolymer (COC) such as TopPac® (Schott, Germany), and the following conditions are fulfilled:
  i) the syringe body has a nominal volume in the range from 15 to 25 ml, optionally in the range from 15.5 to 22.5 ml, and optionally on the range from 19 to 21 ml;
  ii) the syringe body has a barrel length GL in the range from 115 to 140 mm, optionally in the range from 120 to 135 mm, and optionally in the range from 125 to 130 mm;
  iii) the syringe body has an outside diameter OD in the range from 19 to 23 mm, optionally in the range from 20 to 22 mm, and optionally in the range from 21.4 to 21.8 mm.

According to a ninth particular embodiment of the above-described 21$^{st}$ embodiment of holding structure 1 according to the present invention, the primary packaging container is a polymer syringe body, optionally a syringe body made from a cyclic olefin copolymer (COC) such as TopPac® (Schott, Germany), and the following conditions are fulfilled:
  i) the syringe body has a nominal volume in the range from 40 to 60 ml, optionally in the range from 45 to 55 ml, and optionally on the range from 48 to 52 ml;
  ii) the syringe body has a barrel length GL in the range from 125 to 150 mm, optionally in the range from 130 to 145 mm, and optionally in the range from 134 to 140 mm;
  iii) the syringe body has an outside diameter OD in the range from 28 to 35 mm, optionally in the range from 30 to 33 mm, and optionally in the range from 31 to 32 mm.

In a further optional embodiment of holding structure 1 according to the present invention n is at least 20. In this context it is optional that n is selected from the group consisting of 20, 30, 42, 64, 100 and 160. This optional embodiment is a 22$^{nd}$ embodiment of holding structure 1 according to the present invention, that optionally depends on the any of the 1$^{st}$ to the 21$^{st}$ embodiment of the invention.

In a further optional embodiment of holding structure 1 according to the present invention positioning ribs for centering the primary packaging containers in the receptacles are provided at the side walls of the receptacles, which positioning ribs protrude radially inwards into the receptacles and extend in the longitudinal direction of the receptacles. Optionally, these positioning rings are expediently distributed at identical angular spacings relative to each other along the circumference of the side wall, that is to say in particular in a point-symmetrical arrangement. The maximum width $w_1$ of an interior formed by the positioning ribs is slightly greater than a maximum breadth or a maximum external diameter of the containers that are to be received, such that the containers, during their insertion perpendicularly from above into the receptacles, slide without friction, or at any rate with minimal friction, into the receptacles and in doing so are guided to a centered position. This optional embodiment is a 23$^{rd}$ embodiment of holding structure 1 according to the present invention, that optionally depends on any of the 1$^{st}$ to the 22$^{nd}$ embodiments of the invention.

In a further optional embodiment of holding structure 1 according to the present invention m of the n receptacles, in a top view on holding structure, have the shape of parallelograms, optionally the shape of a square or the shape of a rhombus, more optionally the shape of a rhombus, and are arranged in a tightest packing density, with m≤n. In this context it is particularly optional, that the receptacles have the shape of a rhombus and are arranged in such a manner that receptacles that are located horizontally or vertically next to each other share a common corner of the rhombus, and receptacles that are located next to each other on a diagonal share a common edge. The side walls of receptacles that are located next to each other on a diagonal are optionally formed by the same web running in a given (first or second) direction within the outer frame. This optional embodiment is a 24$^{th}$ embodiment of holding structure 1 according to the present invention, that optionally depends on any of the 1$^{st}$ to the 23$^{rd}$ embodiments of the invention.

According to a first particular embodiment of the above-described 24$^{th}$ embodiment of holding structure 1 according to the present invention, the following conditions are fulfilled:
  i) m of the n receptacles have the shape of a square;
  ii) n=42;
  iii) m=20;
  iv) $m_1$ (the weight of the empty holding structure) is in the range from 60 to 80 g, optionally in the range from 64 to 75 g, and optionally in the range from 67 to 71 g.

According to a second particular embodiment of the above-described 24$^{th}$ embodiment of holding structure 1 according to the present invention, the following conditions are fulfilled:
  i) m of the n receptacles have the shape of a rhombus;
  ii) n=64;
  iii) m=42;
  iv) $m_1$ is in the range from 60 to 80 g, optionally in the range from 63 to 75 g, and more optionally in the range from 66 to 70 g.

According to a third particular embodiment of the above-described 24$^{th}$ embodiment of holding structure 1 according to the present invention, the following conditions are fulfilled:
  i) m of the n receptacles have the shape of a rhombus;
  ii) n=100;
  iii) m=80;
  iv) $m_1$ is in the range from 60 to 100 g, optionally in the range from 70 to 90 g, and more optionally in the range from 80 to 86 g.

According to a fourth particular embodiment of the above-described 24$^{th}$ embodiment of holding structure 1 structure according to the present invention, the following conditions are fulfilled:
  i) m of the n receptacles have the shape of a rhombus;
  ii) n=160;
  iii) m=140;
  iv) $m_1$ is in the range from 70 to 110 g, optionally in the range from 80 to 100 g, and optionally in the range from 85 to 91 g.

According to a further optional embodiment of holding structure 1 according to the present invention the holding structure further includes openings that are formed at a number of positions in the base frame as through-holes which can serve in particular as positioning holes in order to allow the possibility that the holding structure can be oriented in a positionally accurate manner on a holding structure receptacle having corresponding positioning pegs or projections, which is, for example, particularly useful during the insertion (nesting), filling, closing or removal (denesting) of the primary packaging containers received in the holding structure. This optional embodiment is a 25$^{th}$ embodiment of holding structure 1 according to the present invention, that optionally depends on the any of the 1$^{st}$ to the 24$^{th}$ embodiment of the invention.

A contribution to solving at least one of the objects according to the invention is also made by a holding structure 2 for simultaneously holding a plurality of primary packaging containers for pharmaceutical, medical or cosmetic compositions;
  wherein the holding structure includes n receptacles for receiving the primary packaging containers, wherein n is an integer having a value of at least 10 and wherein the receptacles are formed by peripherally formed side walls;
  wherein the holding structure includes:
    a flat base frame with a maximum length $L_x$ and a maximum width $L_y$, the flat base frame having a first side and a second side and including a central recess with a length $L'_x$ and a width $L'_y$;
    a plurality of first webs running parallel to each other in a first direction across the central recess;
    a plurality of seconds webs running parallel to each other in a second direction across the central recess;
    wherein the first and seconds webs are arranged in such a manner that they form the side walls of the receptacles, wherein m of the n receptacles, in a top view on holding structure, have the shape of parallelograms, optionally the shape of a square or the shape of a rhombus, optionally the shape of a rhombus, and are arranged in a tightest packing density, with m≤n. In this context it is particularly optional, that the receptacles have the shape of a rhombus and are arranged in such a manner that receptacles that are located horizontally or vertically next to each other share a common corner of the rhombus, and receptacles are located next to each other on a diagonal share a common edge. The side walls of receptacles that are located next to each other on a diagonal are optionally formed by the same web running in a given (first or second) direction within the outer frame.

Optional embodiments of this holding structure are characterized by those features which have been previously described in connection with anyone of the 1$^{st}$ to the 25$^{th}$ embodiments of holding structure 1 according to present invention.

The present invention also provides a plurality of holding structures 1 or 2 according to the present invention, optionally a plurality of holding structures 1 according to any one of the above-described 1$^{st}$ to 25$^{th}$ embodiments, wherein each holding structure in an empty state has a deflection $D_0$ as determined by the test method disclosed herein, and wherein the variance Var $[D_0]$ of the deflection $D_0$ within the plurality of holding structures is less than 0.1, optionally less than 0.05, and optionally less than 0.01.

The variance Var $[D_0]$ of deflection Do is optionally defined as $$\text{Var}[D_0] = \frac{1}{N}\sum_{i=1}^{N}(D_{0i} - \overline{D}_0)^2$$

wherein
  N is the number of holding structures in the plurality of holding structures;
  $D_{0i}$ is the deflection of a given holding structure in the plurality of holding structures;
  $\overline{D_0}$ is the arithmetic mean (average) value of the deflection Do within the plurality of holding structures.

"A plurality of holding structures" in the sense of the present invention optionally includes at least 10 holding structures, optionally at least 25 holding structures, optionally at least 50 holding structures, optionally at least 75 holding structures, and optionally at least 100 holding structures. Furthermore, the plurality of holding structures optionally has been collected arbitrarily and particularly has not been selected with regard to any property.

According to an optional embodiment of the plurality of holdings structures, each holding structure when being loaded with n empty or at least partially filled receptacles having a total weight of up to 400 g has a deflection D as determined by the test method disclosed herein, wherein the variance Var [D] of the deflection D within the plurality of holding structures is less than 0.1, optionally less than 0.05, and optionally less than 0.01.

According to a further optional embodiment of the plurality of holding structures, each holding structure when being loaded with n empty or at least partially filled receptacles having a total weight of up to 800 g has a deflection D' as determined by the test method disclosed herein, wherein the variance Var [D'] of the deflection D' within the plurality of holding structures is less than 0.1, optionally less than 0.05, and optionally less than 0.01.

According to a further optional embodiment of the plurality of holding structures, each holding structure when being loaded with n empty or at least partially filled receptacles having a total weight of up to 1,100 g has a deflection D" as determined by the test method disclosed herein, wherein the variance Var [D"] of the deflection D" within the plurality of holding structures is less than 0.1, optionally less than 0.05 and optionally less than 0.01.

The present invention also provides a transport or packaging container with a plurality of primary packaging containers received therein for substances for pharmaceutical, medical or cosmetic applications, wherein the transport or packaging container is of a box-shaped configuration, wherein a holding structure 1 or 2 according to the present invention, optionally a holding structure 1 according to any one of the above-described $1^{st}$ to $25^{th}$ embodiments, which has the plurality of primary packaging containers held thereon is received in the box-shaped transport or packaging container in order to hold the plurality of primary packaging containers in the transport or packaging container. In this context it is optional that the transport or packaging container is closed or sealed in particular by way of a gas-permeable plastic film, in particular by way of a plastic film which is formed from a gas-permeable braid of plastic fibres and is in particular a Tyvek® film, in order to allow a sterilization of the primary packaging containers by the inflow of a gas through the gas-permeable plastic film.

For sterile transport and storage, there can further be provided a sterile packaging structure having at least one transport unit, as stated above, or having at least one transport or packaging container, as stated above, and having the containers or devices received therein, wherein the at least one transport unit or the at least one transport or packaging container is received in at least one sterile outer packaging bag and is packaged in a sterile manner with respect to the surroundings. Here, the at least one sterile outer packaging bag can have a gas-permeable portion which is formed in particular by a braid of plastic fibres, such as, for example, polypropylene fibres (PP).

The present invention also provides the use of a holding structure 1 or 2 according to the present invention, optionally of a holding structure 1 according to any one of the above-described $1^{st}$ to $25^{th}$ embodiment, to hold a plurality of primary packaging containers for pharmaceutical, medical or cosmetic compositions.

Measurement Methods

The following measurement methods are to be used in the context of the invention. Unless otherwise specified, the measurements have to be carried out at an ambient temperature of 23° C., an ambient air pressure of 100 kPa (0.986 atm), and a relative atmospheric humidity of 50%.

Determination of the Deflection

The deflection $D_0$, D, D' and D" were determined as described in Annex B of ISO 11040-7 ($1^{st}$ edition; 2015 Apr. 1).

For the measurements, the holding structure was placed on a holder, which supports the holding structure in each corner (see FIGS. 11A and 11B).

The holder includes four columns 115 with a diameter of 1.5 cm located at the corners of a plate 114. Columns 115 are spaced apart in such a way that, when a holding structure 100 (empty or filled with receptacles) is placed with the corners on the four columns 115, each column 115 has a horizontal distance y to the longer outer edge of 1.7 cm and a vertical distance x to the shorter outer edge of 1.35 cm (see FIG. 11B). First, the height h1 at the corners of the holding structure 100 resting on the columns 115 is determined with a depth gauge at the points marked with a cross in a circle as shown in FIG. 11B (where h1 corresponds to the mean value of the four measuring points 116). Then the height h2 at the geometric middle of the second side 104b of support structure 100 is determined with a depth gauge, whereby this measuring point 116 is also marked with a cross in a circle in FIG. 11B. The distortion corresponds to the height difference determined as |h1-h2|. If there is no part of a web in the geometric middle of the holding structure at which the height can be determined, the point of a web is chosen for the determination of h2 which is closest to the geometric middle of the second side 104b of support structure 100.

Determination of the Warpage

Warpage was determined by way of the set up used to determine the deflection.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

DETAILED DESCRIPTION OF THE INVENTION

Figure 1:
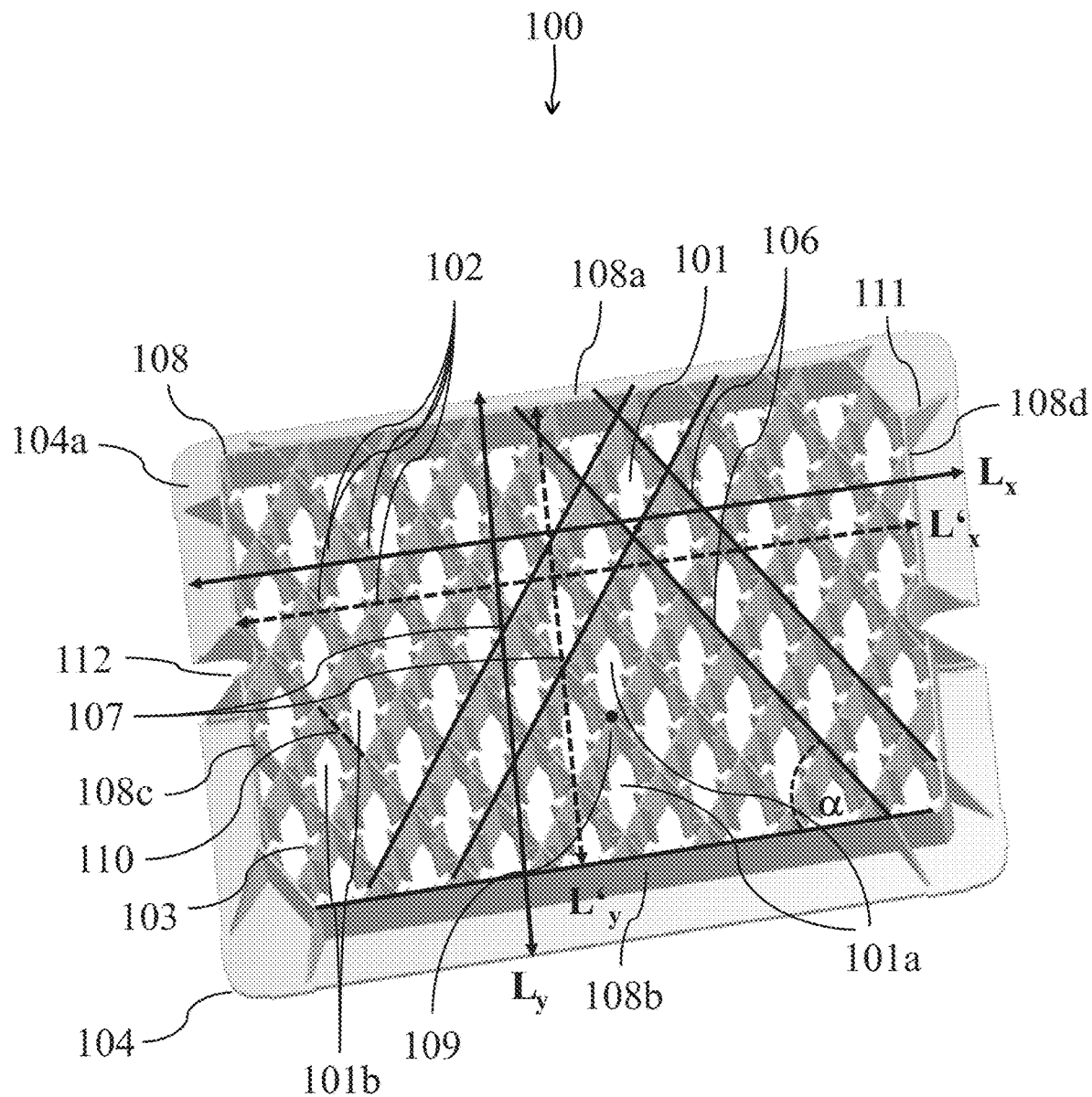
FIG. 1 shows an optional embodiment of the holding structure 100 according to the present invention in a three-dimensional top view.
Figure 5:
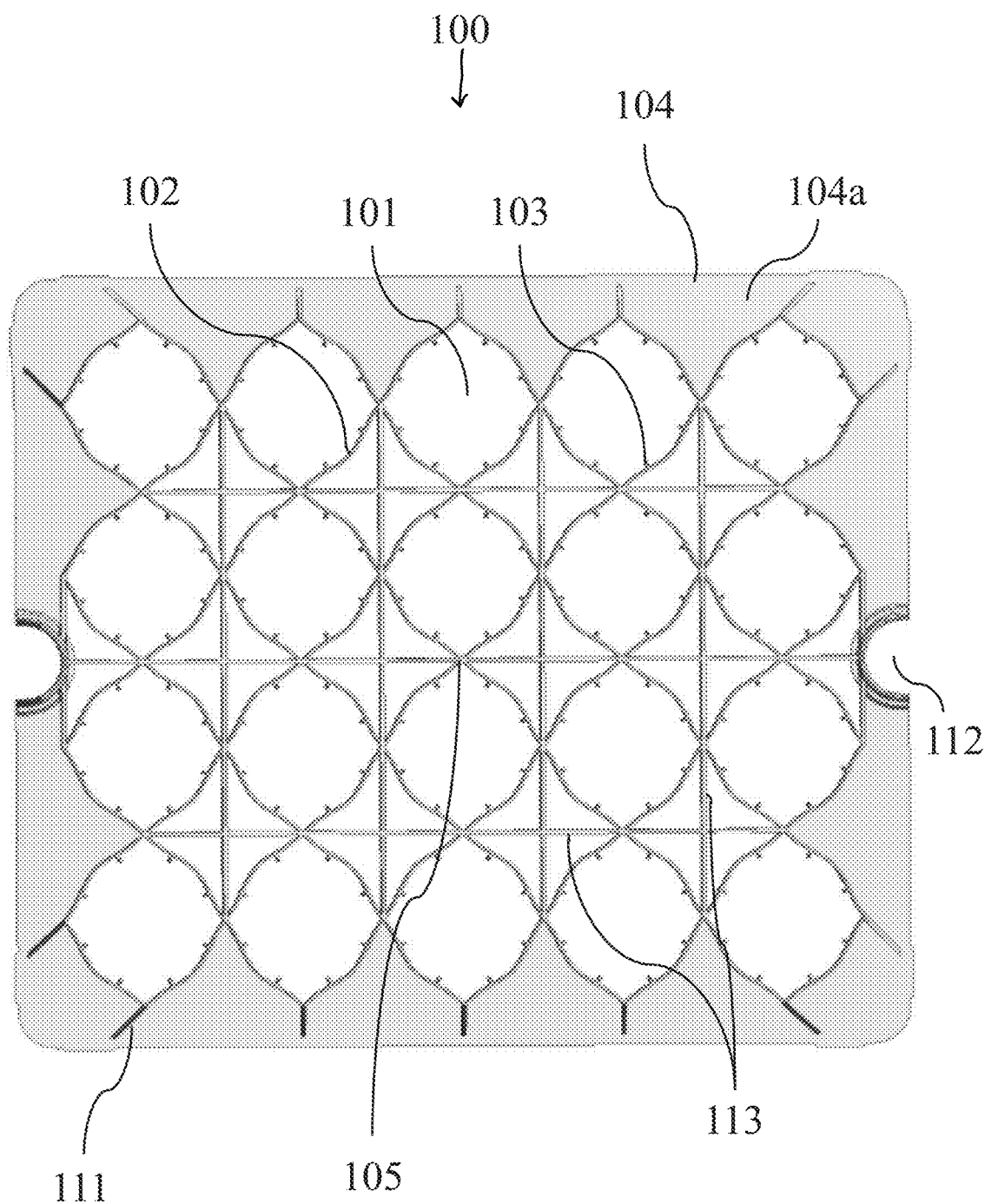
FIG. 5 shows a holding structure 100 according to the present invention for holding 20 primary packaging containers in a top view.

FIG. 1 shows an optional embodiment of the holding structure 100 according to the present invention in a three-dimensional top view. The holding structure 100 as shown in FIG. 1 includes 64 receptacles 101 (from which 42 have the shape of a rhombus) for receiving the primary packaging containers 200, wherein the receptacles 101 are formed by peripherally formed side walls 102. According to the optional embodiment shown in FIG. 1 positioning ribs 103 for centering the primary packaging containers 200 in the receptacles 101 are provided at the side walls 102 of the receptacles 101, which positioning ribs 103 protrude radially inwards into the receptacles 101 and extend in the longitudinal direction of the receptacles 101. In the optional embodiment of the holding structure 100 shown in FIG. 11 the holding structure 100 further includes a flat base frame 104 having a first side 104a and a second side 104b (not visible in the view shown in FIG. 1) and including a central recess 105 (this central recess corresponds to the white area within the flat base frame which is not completely visible as it is partially covered by the first and second webs 106, 107 running through the central recess 105; the central recess 105, however, is better visible in the holding structure as shown in FIG. 5). The holding structure 100 further includes an outer frame 108 that protrudes from the flat base frame 104 on the first side 104a, on the second side 104b or on both sides 104a, 104b (in FIG. 1 the outer frame only protrudes from the flat base frame from the first side 104a) and that is connected with the flat base frame 104 in such a manner that the outer frame 108 surrounds the central recess of the base frame 104. The holding structure further includes a plurality of first webs 106 running parallel to each other in a first direction within the outer frame 108, wherein each of the first webs 106 is connected to the outer frame 108 at its respective ends, and a plurality of seconds webs 107 running parallel to each other in a second direction within the outer frame 108, wherein each of the second webs 107 is also connected to the outer frame 108 at its respective ends. As can be seen in FIG. 1, the first and seconds webs 106, 107 are arranged in such a manner that they form the side walls 102 of the receptacles 101, wherein 42 of the 64 receptacles 102, in a top view of holding structure 100, have the shape of a rhombus and are arranged in a tightest packing density. Such a tightest packaging density is characterized in that receptacles 101a that are located vertically (or horizontally) next to each other share a common corner 109 of the parallelogram (which in the case of the holding structure shown in FIG. 1 is a rhombus), and receptacles 101b that are located next to each other on a diagonal share a common edge 110 of the parallelogram.

As also shown in FIG. 1, the holding structure according to the present invention may further include stabilizing elements 111 by way of which the outer frame 108 is connected to the flat base frame 104. Optionally, these stabilizing elements 111 are in the form of wings, which are connected to the edges 108a, 108b, 108c and 108d of the outer frame 108 on one side and to the flat base frame on an adjacent side of the stabilizing element 111. In this context, it is also optional that each edge 108a, 108b, 108c 108d of the outer frame 108 is connected to the flat base frame 104 via at least two such stabilizing elements 111. As can also be seen in FIG. 1, the holding structure 100 may further include access openings 112 that enable the holding structure 100 to be gripped or guided. Optionally, the holding structure includes two such access openings 112 recessed into the flat base frame 104 on opposite sides of the holding device 100.

Figure 2:
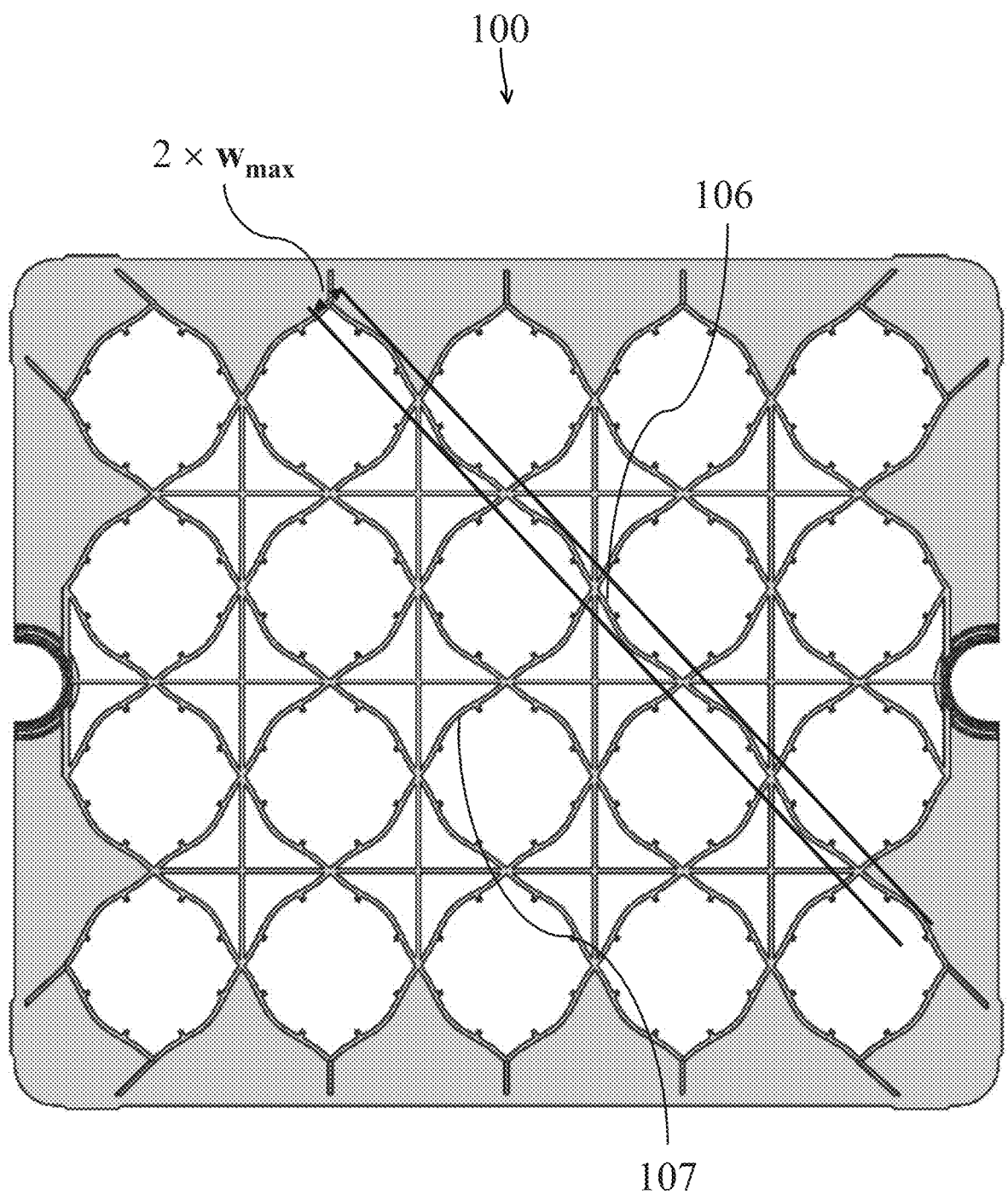
FIG. 2 shows the determination of the maximum waviness $w_{max}$ using a holding structure 100 according to the present invention for holding 20 primary packaging containers.

FIG. 2 shows the determination of the maximum waviness $w_{max}$ using a holding structure 100 according to the present invention for holding 20 primary packaging containers 200 (as shown in FIG. 5). As can be seen in FIG. 2, for the determination of $w_{max}$ two straight lines, which are parallel to each other, are applied to the web (106, 107), which may be wavelike, whereby one straight line touches the web at the crests of the waves and the other straight line touches the web at the troughs of the waves. The "waviness" corresponds to half the distance between these two straight lines.

Figure 3:
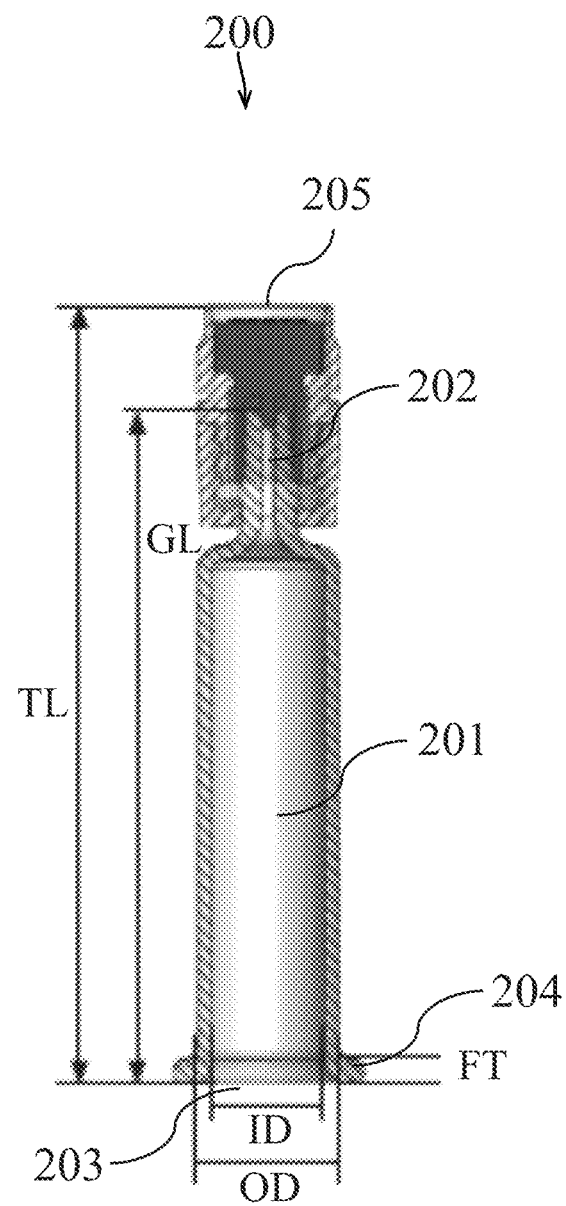
FIG. 3 shows a syringe 200 that can be held by the holding structure 100 according to the present invention in a side view.

FIG. 3 shows a syringe 200 that can be held by the holding structure 100 according to the present invention in a side view. The syringe optionally includes a glass syringe or a polymer syringe body 201 on whose distal end there is formed an ejection opening 202 and, on the opposite end, a filling opening 203 for filling and subsequently receiving a plunger or stopper, wherein at this opposite end a widened flange 204 is provided. In the syringe shown in FIG. 2 the ejection opening 202 is closed by way of a cap 205. Such syringes are obtainable by the Schott AG, Germany ("syriQ® Luer Lock SRC® Syringes" or, "syriQ® Luer Lock OVS® Syringes" or "syriQ® Luer Cone Syringes" or TopPac® syringes). However, the holding structure 100 according to the present invention is also suitable to hold syringes that include a needle at the ejection opening 202 (such as the "syriQ® Staked Needle Syringes" or the "syriQ® BioPure® Syringes" that are obtainable by the Schott AG, Germany), wherein this needle is optionally protected by suitable needle caps. As can be seen in FIG. 2, the syringes are characterized by a total length TL, a barrel length GL, an inner diameter ID, an outer diameter OD and a flange thickness FT.

Figure 4:
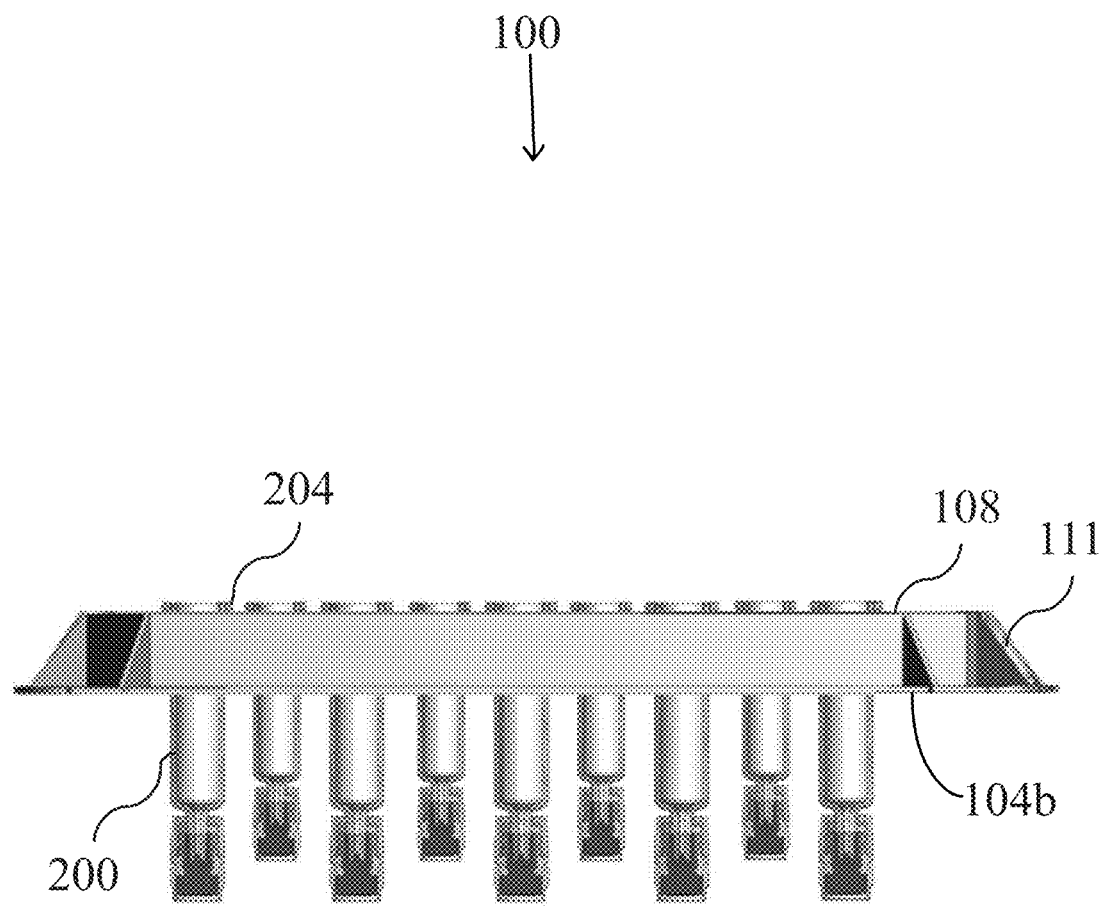
FIG. 4 shows the holding structure 100 according to the present invention that is holding syringes bodies 200 in a side view.

FIG. 4 shows the holding structure 100 according to the present invention that is holding syringes 200 in a side view. As can be seen in that figure, it is optional that the syringes 200 are received upside down in the receptacles 101 of the holding structure 100 according to the present invention, wherein the widened flange 204 lies on the upper ends of the side walls 102 formed by the first and the second webs 106, 107.

FIG. 5 shows a holding structure 100 according to the present invention for holding 20 primary packaging containers 200, optionally 20 syringes, in a top view. In contrast to the holding structures shown in FIGS. 7, 8, 9 and 10 (in which the side walls 102 of the receptacle 101 are formed by continuous straight webs 106, 107 having no (or almost no) waviness), the side walls 102 are designed here in the form of curved webs, slightly bulging in the middle, which run at an angle of about 45° inside stabilizing ribs 113 stretched within the central recess 105 like a chess board.

Figure 6:
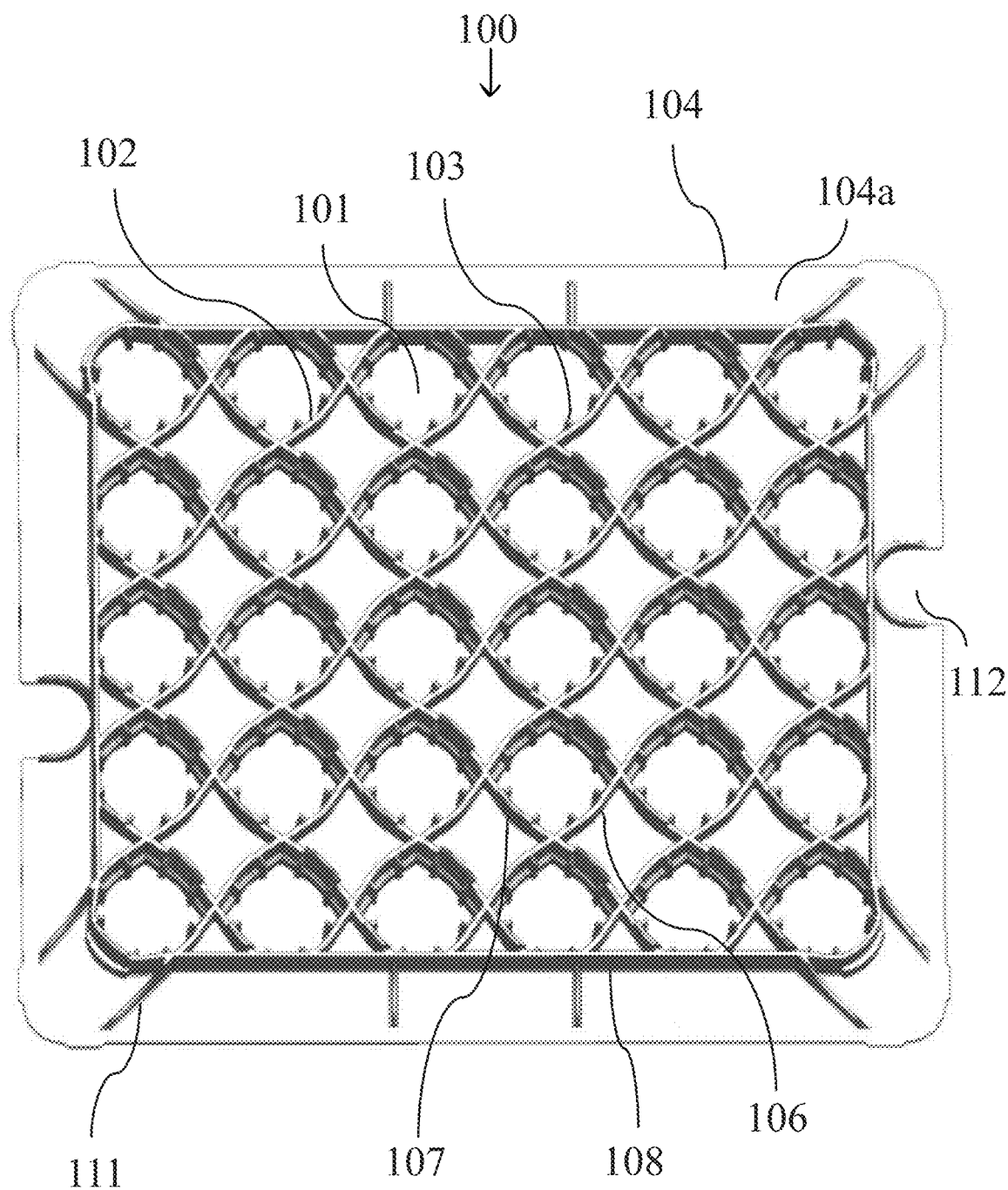
FIG. 6 shows a holding structure 100 according to the present invention for holding 30 primary packaging containers in a top view.

FIG. 6 shows a holding structure 100 according to the present invention for holding 30 primary packaging containers, optionally 30 syringes, in a top view. As in the holding structure 100 shown in FIG. 5 the side walls 102 are also designed in the form of curved webs, slightly bulging in the middle. However, the waviness of webs 106, 107 forming the side walls 102 of the receptacle 101 is less pronounced compared to the holding structure shown in FIG. 5. However, in contrast to the design shown in FIG. 5 webs 106, 107 are stretched inside an outer frame 108. As a further difference to the holding structures 100 shown in FIGS. 1, 8, 9 and 10, the receptacles 101 in the holding structure 100 shown in FIG. 6 are not arranged in a tightest packing density.

Figure 7:
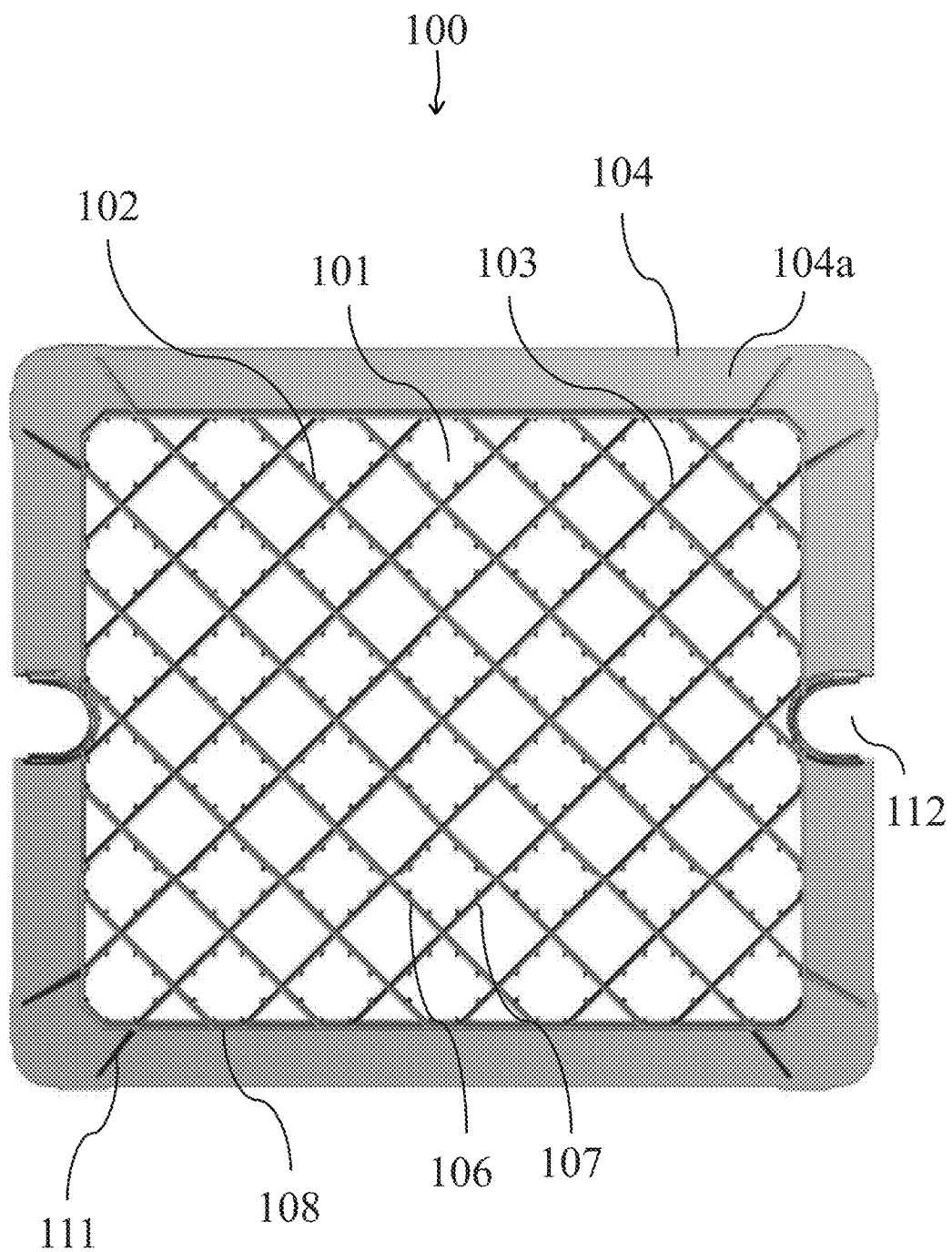
FIG. 7 shows a holding structure 100 according to the present invention for holding 42 primary packaging containers in a top view.

FIG. 7 shows a holding structure 100 according to the present invention for holding 42 containers. In contrast to the designs shown in FIGS. 5 and 6, the side walls 102 of the receptacles 101 are formed by continuous and straight webs 106, 107 stretched inside the outer frame 108 and having no (or almost no) waviness. In the embodiment shown in FIG. 7 the receptacles have the shape of squares, wherein—as in FIG. 6—the receptacles 101 in the holding structure 100 are also not arranged in a tightest packing density (because the holding structure includes square-shaped recesses in which no positioning ribs 103 are arranged and which are not intended to receive primary packaging containers 200).

Figure 8:
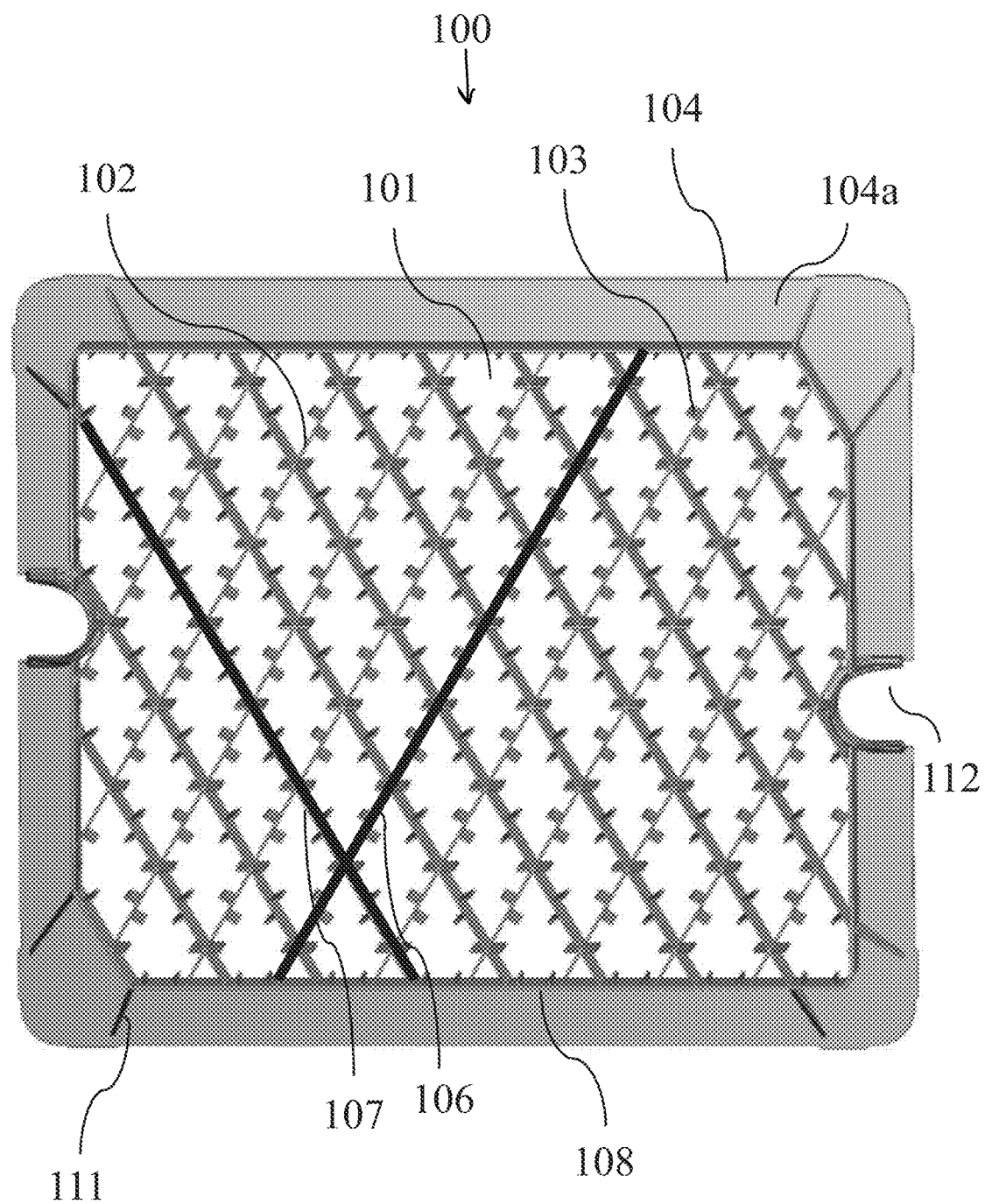
FIG. 8 shows a holding structure 100 according to the present invention for holding 64 primary packaging containers in a top view.
Figure 9:
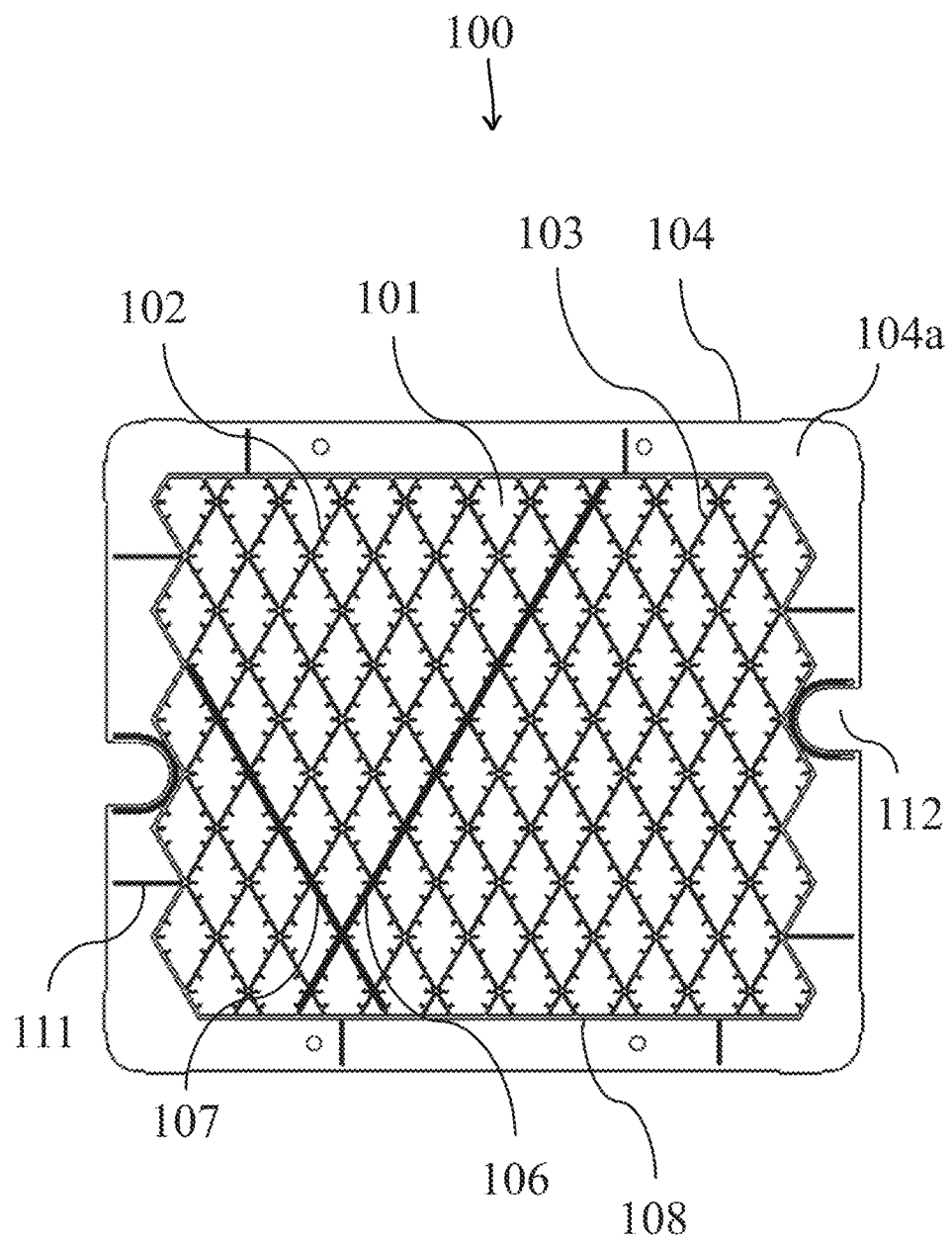
FIG. 9 shows a holding structure 100 according to the present invention for holding 100 primary packaging containers in a top view.
Figure 10:
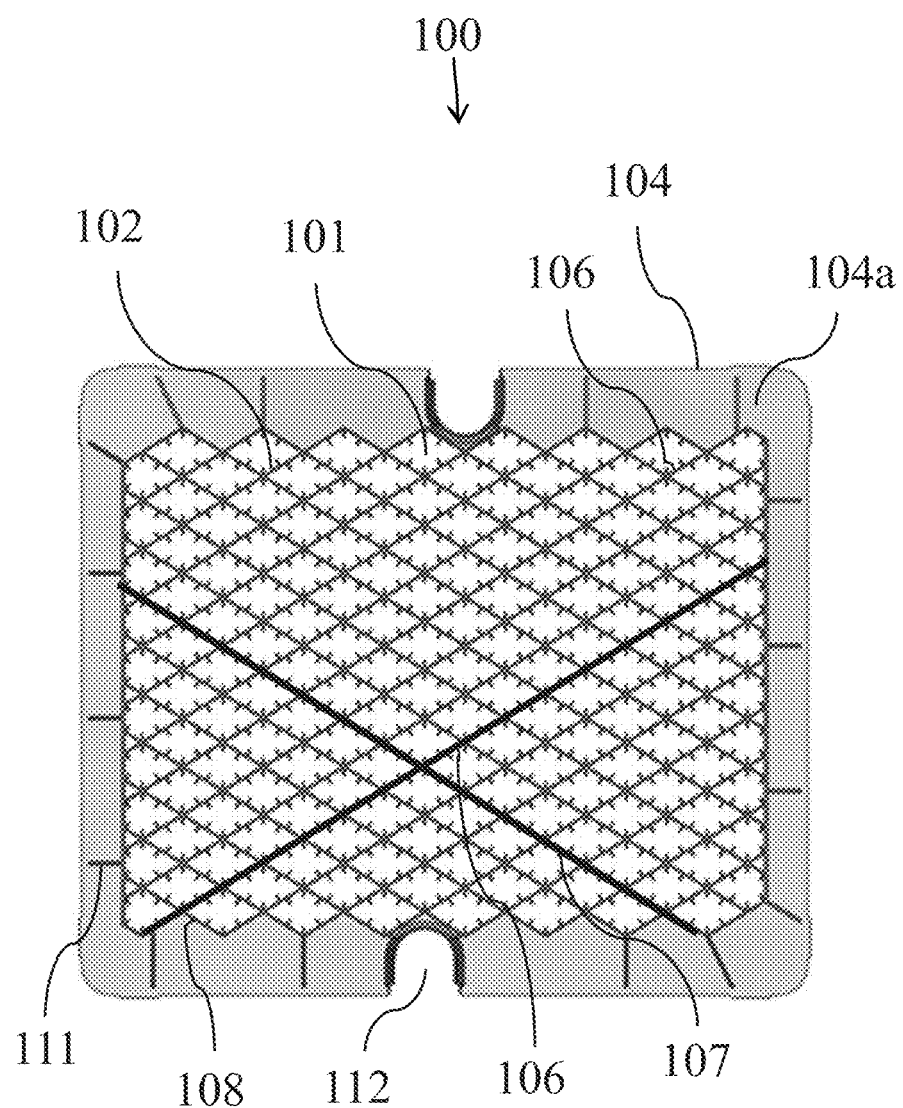
FIG. 10 shows a holding structure 100 according to the present invention for holding 160 primary packaging containers in a top view.

FIGS. 8, 9 and 10 show optional holding structures 100 according to the present invention for holding 64 (FIG. 8), 100 (FIG. 9) and 160 (FIG. 10) primary packaging containers 200, in a top view. As can be seen in these figures, the holding structure 100 includes a plurality of first webs 106 running parallel to each other in a first direction (i.e., from the left on the bottom to the right on the top) within the outer frame 108, wherein each of the first webs 106 is connected to the outer frame 108 at its respective ends. The holding structure 100 further includes plurality of seconds webs 107 running parallel to each other in a second direction (i. e. from the right on the bottom to the left on the top) within the outer frame 108, wherein each of the second webs 107 is also connected to the outer frame 108 at its respective ends (in FIGS. 8, 9 and 10 only one of these first and second webs—indicated by a bold line—is identified by its reference number). As can be seen in FIGS. 8, 9 and 10 the first and seconds webs 106, 107 are arranged in such a manner that they form the side walls 102 of the receptacles 101, wherein at least some of the receptacles 102, in a top view on holding structure 100, have the shape of a rhombus and are arranged in a tightest packing density.

Figure 11A:
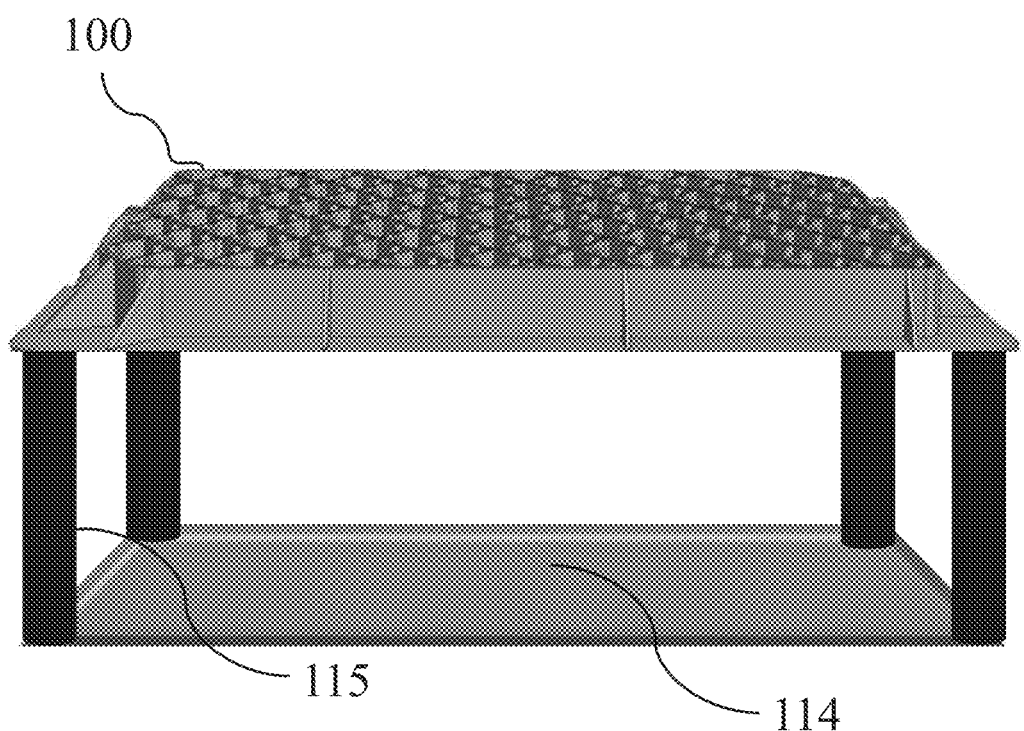
FIGS. 11A and B show the experimental setup for determining deflection D' and D" of the holding structure 100 according to the present invention.
Figure 11B:
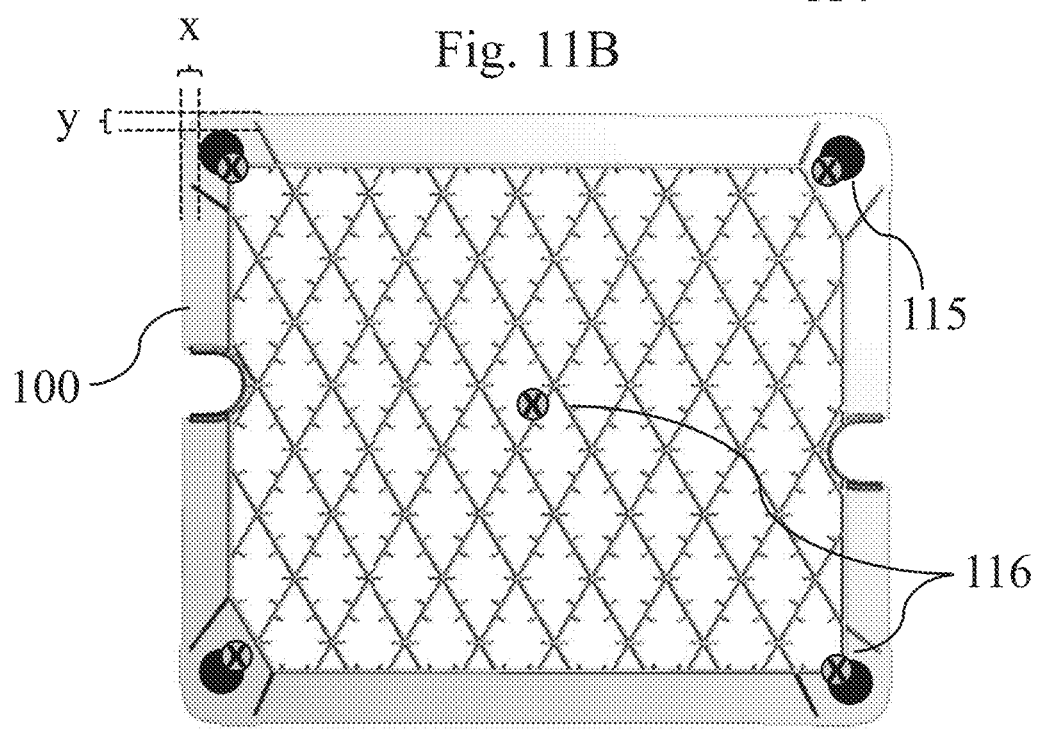
Figure 12:
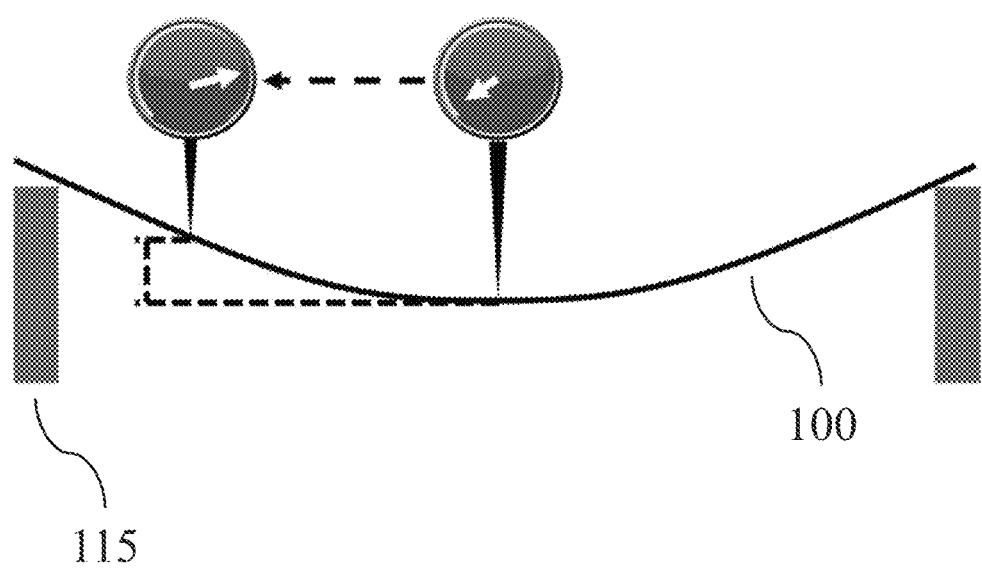
FIG. 12 also shows the determination of deflection D' and D" of the holding structure 100 according to the present invention in a side view.

FIGS. 11A, 11B and 12 show the experimental setup for determining deflection D, D' and D" of the holding structure 100 according to the present invention. As can be seen, the device for determining the deflection of a holding structure 100 is a holder that includes a base plate 114 and four columns 115 on which the holding structure 100 is placed at the four corners. For the measurements, the holding structure 100 is placed on the holder. With a depth gauge, the height differences between the middle of the holding structure 100 and the four corners were determined.

Figure 13A:
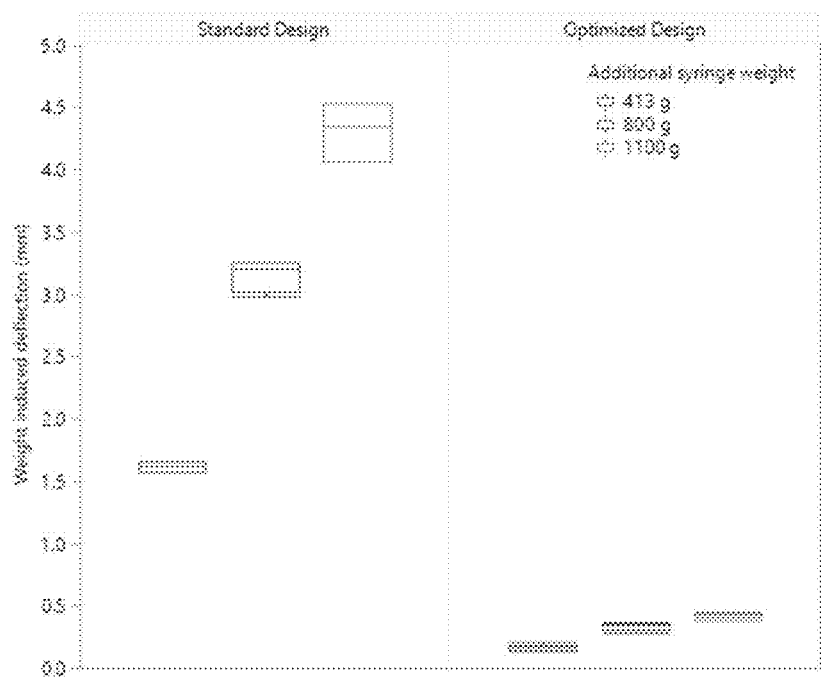
FIGS. 13A and B show the deflection D, D' and D" of a holding structure known from the prior art as shown in FIG. 13B (left side of FIG. 13A) and of a holding structure 100 according to the present invention as shown in FIG. 6 (right side of FIG. 13A).
Figure 13B:
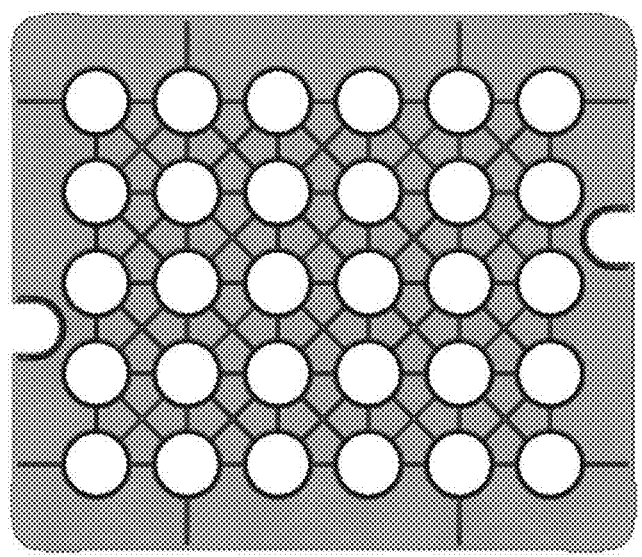

FIG. 13A shows the deflection D, D' and D" of a holding structure known from the prior art (shown in FIG. 13B) that does not include first and the second webs in the form of a continuous beam having a defined maximum waviness $w_{max}$, wherein the first and seconds webs are arranged in such a manner that they form the side walls of receptacles (left side of FIG. 13A; n=30) and of a holding structure 100 according to the present invention as shown in FIG. 6 (n=30; $w_{max}$=2 mm). Both nests are filled with 30 empty syringes (additional syringe weight=413 g), half-filled syringes (additional syringe weight=800 g) or full-filled filled syringes (additional syringe weight=1,100 g). The syringes used are syriQ® Luer Lock TC Syringes, 20 ml (Schott AG, Germany). As can be seen in FIG. 13A, a reduction of the waviness helps to significantly reduce the deflection of the nest if it is filled with empty, half-filled, or fully-filled syringes.

LIST OF REFERENCE SIGNS 100 holding structure
101 receptacles
101a receptacles that are located vertically or horizontally next to each
101b receptacles that are located next to each other on a diagonal
102 side walls forming the receptacles
103 positioning ribs
104 flat base frame having a first side 104a and a second side 104b
104a first side of the base frame 104
104b second side of the base frame 104
105 central recess
106 first webs
107 second webs
108 outer frame
108a top edge of the outer frame 108
108b bottom edge of the outer frame 108
108c first side edge of the outer frame 108
108d second side edge of the outer frame 108
109 common corner
110 common edge
111 stabilizing element
112 access opening
113 stabilizing ribs
114 base plate
115 column on which the holding structure is place at the corner
116 measuring point for determining the heights of the holding structure
200 container that can be held by the holding structure, optionally a syringe, optionally a pre-filled syringe that is a ready to be used
201 syringe body
202 ejection opening
203 filling opening
204 flange
205 closure system, optionally a cap While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A holding structure for simultaneously holding a plurality of primary packaging containers for a plurality of pharmaceutical, medical, or cosmetic compositions, the holding structure comprising:
a plurality of receptacles configured for receiving the plurality of primary packaging containers, a total number of the plurality of receptacles being a number n, which is an integer having a value of at least 10, the plurality of receptacles being formed by a plurality of side walls which are peripherally formed;
a flat base frame including a maximum length $L_x$, a maximum width $L_y$, a first side, a second side, and a central recess with a length $L'_x$ and a width $L'_y$;
a plurality of first webs running parallel to each other in a first direction across the central recess; and a plurality of second webs running parallel to each other in a second direction across the central recess, the plurality of first webs and the plurality of second webs being arranged in such a manner that the plurality of first webs and the plurality of second webs form the plurality of side walls of the plurality of receptacles, each of the plurality of first webs and the plurality of second webs being formed as a continuous beam having a maximum waviness $w_{max}$ of 4.0 mm, wherein the holding structure includes a warpage of less than 2.0 mm as determined by a test method before a steam sterilization, the warpage corresponding to a bending of the holding structure after the holding structure has been prepared and when the holding structure is empty.

2. The holding structure according to claim 1, wherein the holding structure is configured for being used in the test method to determine the warpage of the holding structure, the test method including the steps of:

providing a device configured for determining the warpage of the holding structure, the device being a holder that includes a base plate and a plurality of columns coupled with the base plate;

placing the holding structure on the plurality of columns; and determining, with a depth gauge, any difference in a height between a middle portion of the holding structure and at least one corner of the holding structure.

3. The holding structure according to claim 1, wherein the warpage is less than 1.0 mm.

4. The holding structure according to claim 1, wherein the warpage is less than 0.5 mm.

5. The holding structure according to claim 1, wherein the holding structure is configured for being prepared by way of 3D-printing, injection molding, or a combination of 3D-printing and injection molding.

6. A holding structure for simultaneously holding a plurality of primary packaging containers for a plurality of pharmaceutical, medical, or cosmetic compositions, the holding structure comprising:

a plurality of receptacles configured for receiving the plurality of primary packaging containers, a total number of the plurality of receptacles being a number n, which is an integer having a value of at least 10, the plurality of receptacles being formed by a plurality of side walls which are peripherally formed;

a flat base frame including a maximum length $L_x$, a maximum width $L_y$, a first side, a second side, and a central recess with a length $L'_x$ and a width $L'_y$;

a plurality of first webs running parallel to each other in a first direction across the central recess; and a plurality of second webs running parallel to each other in a second direction across the central recess, the plurality of first webs and the plurality of second webs being arranged in such a manner that the plurality of first webs and the plurality of second webs form the plurality of side walls of the plurality of receptacles, each of the plurality of first webs and the plurality of second webs being formed as a continuous beam having a maximum waviness $w_{max}$ of 4.0 mm, wherein the holding structure includes a warpage of less than 4.0 mm as determined by a test method after a steam sterilization at 122° C. for 22 minutes, the warpage corresponding to a bending of the holding structure after the holding structure has been prepared and when the holding structure is empty.

7. The holding structure according to claim 6, wherein the holding structure is configured for being used in the test method to determine the warpage of the holding structure, the test method including the steps of:

providing a device configured for determining the warpage of the holding structure, the device being a holder that includes a base plate and a plurality of columns coupled with the base plate;

placing the holding structure on the plurality of columns; and determining, with a depth gauge, any difference in a height between a middle portion of the holding structure and at least one corner of the holding structure.

8. The holding structure according to claim 6, wherein the warpage is less than 2.0 mm.

9. The holding structure according to claim 6, wherein the warpage is less than 1.0 mm.

* * * * *